United States Patent
Ali et al.

(10) Patent No.: US 6,692,487 B2
(45) Date of Patent: Feb. 17, 2004

(54) CRYOSURGICAL MONITORING SYSTEM

(75) Inventors: Jawahar M. Ali, Mission Viejo, CA (US); Sanford D. Damasco, Irvine, CA (US); Thach Duong, Garden Grove, CA (US)

(73) Assignee: Endocare, Inc., Irvine, CA (US)

( * ) Notice: Subject to any disclaimer, the term of this patent is extended or adjusted under 35 U.S.C. 154(b) by 15 days.

(21) Appl. No.: 10/057,338

(22) Filed: Jan. 23, 2002

(65) Prior Publication Data

US 2003/0139738 A1 Jul. 24, 2003

(51) Int. Cl.[7] .............................................. A61B 18/18
(52) U.S. Cl. ......................................... 606/20; 128/898
(58) Field of Search ..................... 606/20–26

(56) References Cited

U.S. PATENT DOCUMENTS

| | | | | |
|---|---|---|---|---|
| 4,196,734 A | * | 4/1980 | Harris | 606/31 |
| 4,275,734 A | * | 6/1981 | Mitchiner | 606/23 |
| 4,619,257 A | * | 10/1986 | Linner et al. | 606/20 |
| 4,672,963 A | | 6/1987 | Barken | 128/303.1 |
| 5,147,355 A | * | 9/1992 | Friedman et al. | 606/23 |
| 5,207,674 A | * | 5/1993 | Hamilton | 606/20 |
| 5,531,742 A | | 7/1996 | Barken | 606/21 |
| 5,540,062 A | * | 7/1996 | Maytal | 62/293 |
| 5,603,221 A | * | 2/1997 | Maytal | 62/51.2 |
| 5,647,868 A | * | 7/1997 | Chinn | 606/21 |
| 5,667,505 A | * | 9/1997 | Straus | 606/24 |
| 5,674,218 A | * | 10/1997 | Rubinsky et al. | 606/20 |
| 5,706,810 A | | 1/1998 | Rubinsky | 128/653.1 |
| 5,882,306 A | | 3/1999 | Ramamurthy | 600/440 |
| 6,002,968 A | * | 12/1999 | Edwards | 607/101 |
| 6,083,166 A | | 7/2000 | Holdaway | 600/439 |
| 6,139,544 A | * | 10/2000 | Mikus et al. | 606/21 |
| 6,190,378 B1 | * | 2/2001 | Jarvinen | 606/21 |
| 6,235,018 B1 | * | 5/2001 | LePivert | 606/20 |
| 6,355,029 B1 | * | 3/2002 | Joye et al. | 606/21 |
| 6,432,102 B2 | * | 8/2002 | Joye et al. | 606/21 |

OTHER PUBLICATIONS

Wong, et al. Cryosurgery as a Treatment for Prostate Carcinoma, 79 Cancer 963 (Mar. 1997).
Onik, Ultrasound–Guided Cryosurgery, Scientific American at 62 (Jan. 1996).
Onik, Cohen, et al. Transrectal Ultrasound–Guided Percutaneous Radical Cryosurgical Ablation of the Prostate, 72 Cancer 1291 (1993).

* cited by examiner

*Primary Examiner*—Roy D. Gibson
*Assistant Examiner*—Peter J Vrettakos
(74) *Attorney, Agent, or Firm*—Lawrence N. Ginsberg

(57) ABSTRACT

A software module for a software controlled device for performing cryosurgical procedures on a treatment region with a cryosurgical probe. The software controlled device is of a type that is responsive to user input settings. The software module includes a temperature feedback control system which is adaptive to the external heat load of a treatment region and utilizes user input settings for determining an optimal rate of gas flow through a cryosurgical probe thereby enabling the user to precisely monitor and deliver a cryosurgical treatment.

5 Claims, 3 Drawing Sheets

Temperature Feedback Control System

Gas Tank Monitoring System

US 6,692,487 B2

CRYOSURGICAL MONITORING SYSTEM

BACKGROUND OF THE INVENTION

1. Field of the Invention

The present invention relates to cryosurgical procedures and more particularly to a cryosurgical monitoring system with a temperature feed back control system.

2. Description of the Related Art

In the past, cryosurgical systems have been made to apply extremely low temperatures (i.e. −20° C. to −200° C.) to a small region of treatment in a patient by accurately placing the cryosurgical probe and controlling the rate of cooling applied to the region of treatment. It is possible to ablate the treatment region; however, it is difficult for the user to set the rate of cooling for a given treatment region since the heat load may vary from one treatment region to another. Though the user might know the desired temperature, he may not be able to accurately control the rate of cooling to achieve the desired temperature in the treatment region.

OBJECTS AND SUMMARY OF THE INVENTION

It is therefore a principal object of the present invention to compute the cooling rate based on the desired temperature thus making it easier for the user to achieve the desired temperature at various treatment regions.

This and other objects of the present invention are achieved by the present invention which in a broad aspect, is a software module for a software controlled device for performing cryosurgical procedures on a treatment region with a cryosurgical probe. The software controlled device is of a type that is responsive to user input settings. The software module includes a temperature feedback control system which is adaptive to the external heat load of a treatment region and utilizes user input settings for determining an optimal rate of gas flow through a cryosurgical probe thereby enabling the user to precisely monitor and deliver a cryosurgical treatment.

In another broad aspect, the present invention comprises a cryosurgical monitoring system for use with a cryosurgical probe that receives gas from a gas supply. The cryosurgical monitoring system includes a software controlled device that includes a software module, an electronics module, a pneumatics module and a user interface. The software module provides an interface for monitoring and controlling cryosurgical procedures in response to user input settings and real-time electronics feedback. The software module includes a temperature feedback system which is adaptive to the external heat load of a treatment region and utilizes user input settings for determining an optimal rate of gas flow through a cryosurgical probe thereby enabling the user to precisely monitor and deliver a cryosurgical treatment. The software module provides control data output. The electronics module receives the control data output from the software module and provides the real-time electronics feedback. It also provides an electrical output. The pneumatics module receives the electrical output and provides a pneumatics module output feedback signal to the electronics module. The pneumatics module provides a pneumatic output to a cryosurgical probe. The user interface includes a user input element and a user output element. The user input element provides the user provided settings to the software module.

DETAILED DESCRIPTION OF THE INVENTION

Figure 1:
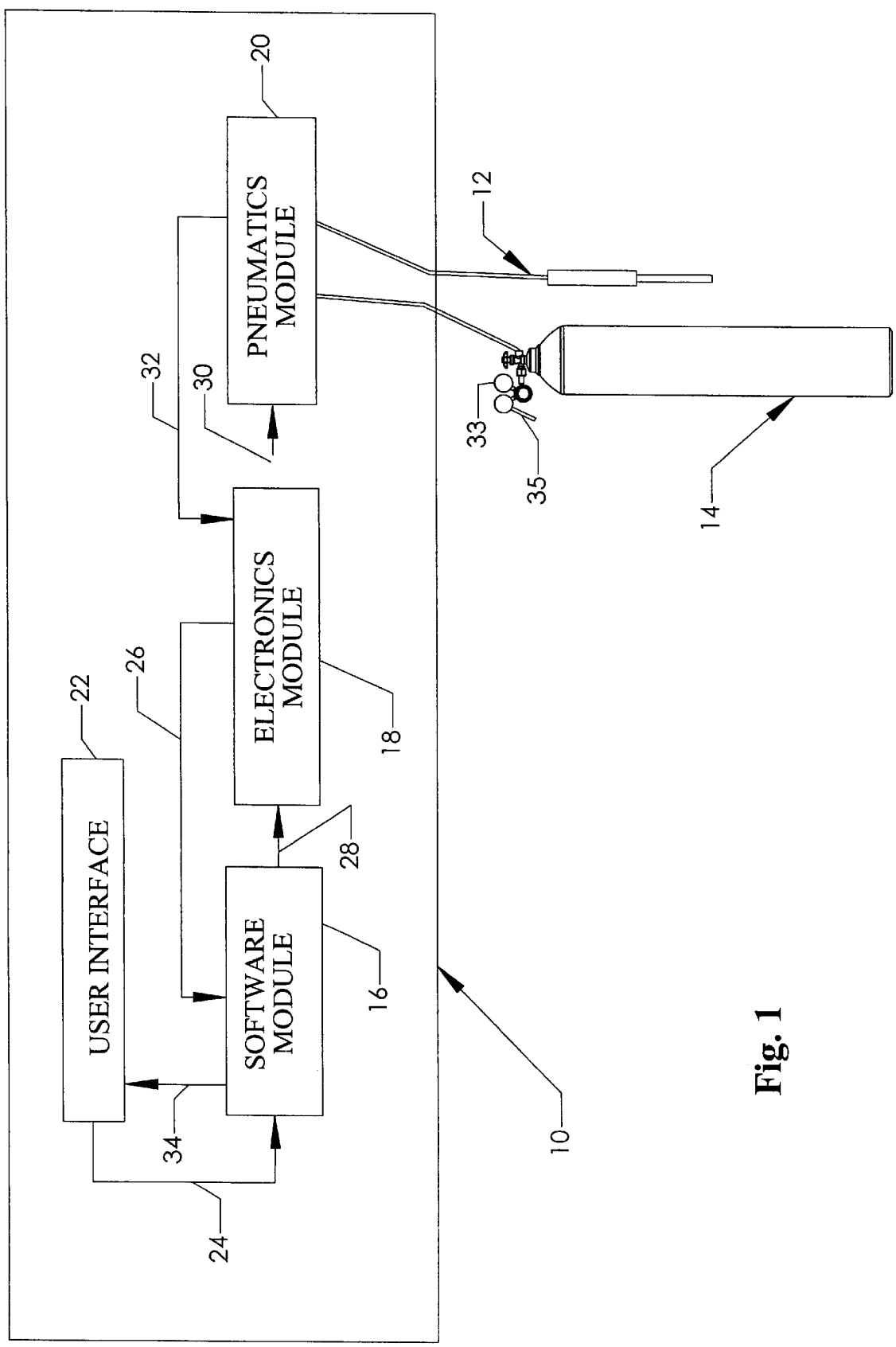
FIG. 1 is a schematic illustration of the cryosurgical monitoring system of the present invention.

Referring to the drawings and the characters of reference marked thereon FIG. 1 illustrates a preferred embodiment of the cryosurgical monitoring system of the present invention, designated generally 10. The cryosurgical monitoring system 10 is shown in relationship with a cryosurgical probe 12 and a gas supply tank 14. The cryosurgical monitoring system 10 comprises a software controlled device for performing cryosurgical procedures. It includes a software module 16, an electronics module 18, a pneumatics module 20 and a user interface 22.

The software module 16 provides an interface for monitoring and controlling cryosurgical procedures in response to user input settings 24 and real-time electronics feedback 26. As will be discussed in detail below, the software module 16 comprises a temperature feedback system that is adaptive to the external heat load of a treatment region of the patient. The software module 16 utilizes the user input settings 24 for determining an optimal rate of gas flow through the cryosurgical probe 12 thereby enabling the user to precisely monitor and deliver a cryosurgical treatment. The software module is developed as a real-time embedded system so that dedicated hardware can be designed and programmed to achieve the desired purpose. The software module may be programmed in C language and loaded into the system memory. A commercially available microcontroller such as an NEC 8-bit microcontroller may be used, for example, as the main processing unit. The software module 16 provides control data output 28 to the electronics module 18. The electronics module 18 receives the control data output 28 from the software module 16 and provides the real-time electronics feedback 26. The electronics module comprises electronic hardware to execute the instructions supplied by the software module. The hardware may include a motherboard for the microcontroller, an 8-bit NEC microcontroller, an Input-Output board for interfacing the motherboard to the Input/Output elements, and hardware for displaying the data on the output element. The output hardware may include, for example, a Vacuum Fluorescent display and a Seven-segment display. The drivers for the displays may also be included in the hardware. The electronics module also includes interface hardware for connecting to the pneumatics module.

The electronics module 18 provides an electrical output 30 to the pneumatics module 20. The pneumatics module 20 provides a pneumatic output to the cryosurgical probe 12 via the pneumatics module 20. It also provides a pneumatics module output feedback signal 32 to the electronics module 18. A regulator element 33 provides the pneumatic output to the cryosurgical probe 12. A pressure sensing element 35 senses gas pressure upstream of the regulator element.

The user interface 22 includes a user input element and a user output element, i.e. display. The user input element provides the user provided settings to the software module 16.

A user interface feedback 34 from the software module 16 to the user interface 22 is used to feed back information to the user regarding time left on the tank, feedback temperature of the cryosurgical probe 12 and appropriate warning signals. The user interface element includes a membrane switch panel for accepting the user inputs for setting the target temperature, the freeze duration, for starting the freeze, for stopping the freeze and to vent the gas from the system.

Figure 2:
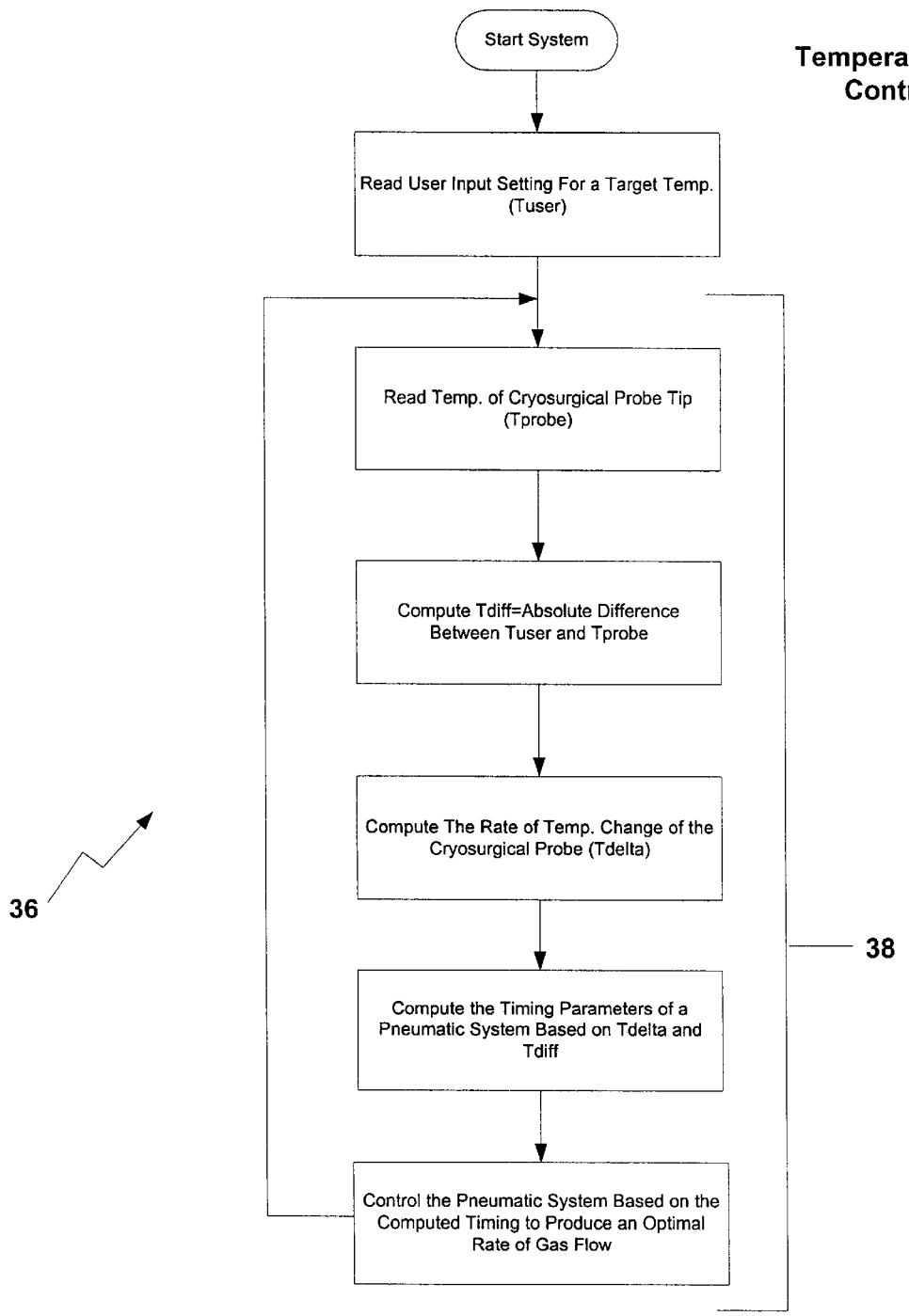
FIG. 2 is a flow diagram of the temperature feedback control system, in accordance with the principles of the present invention.
Figure 3:
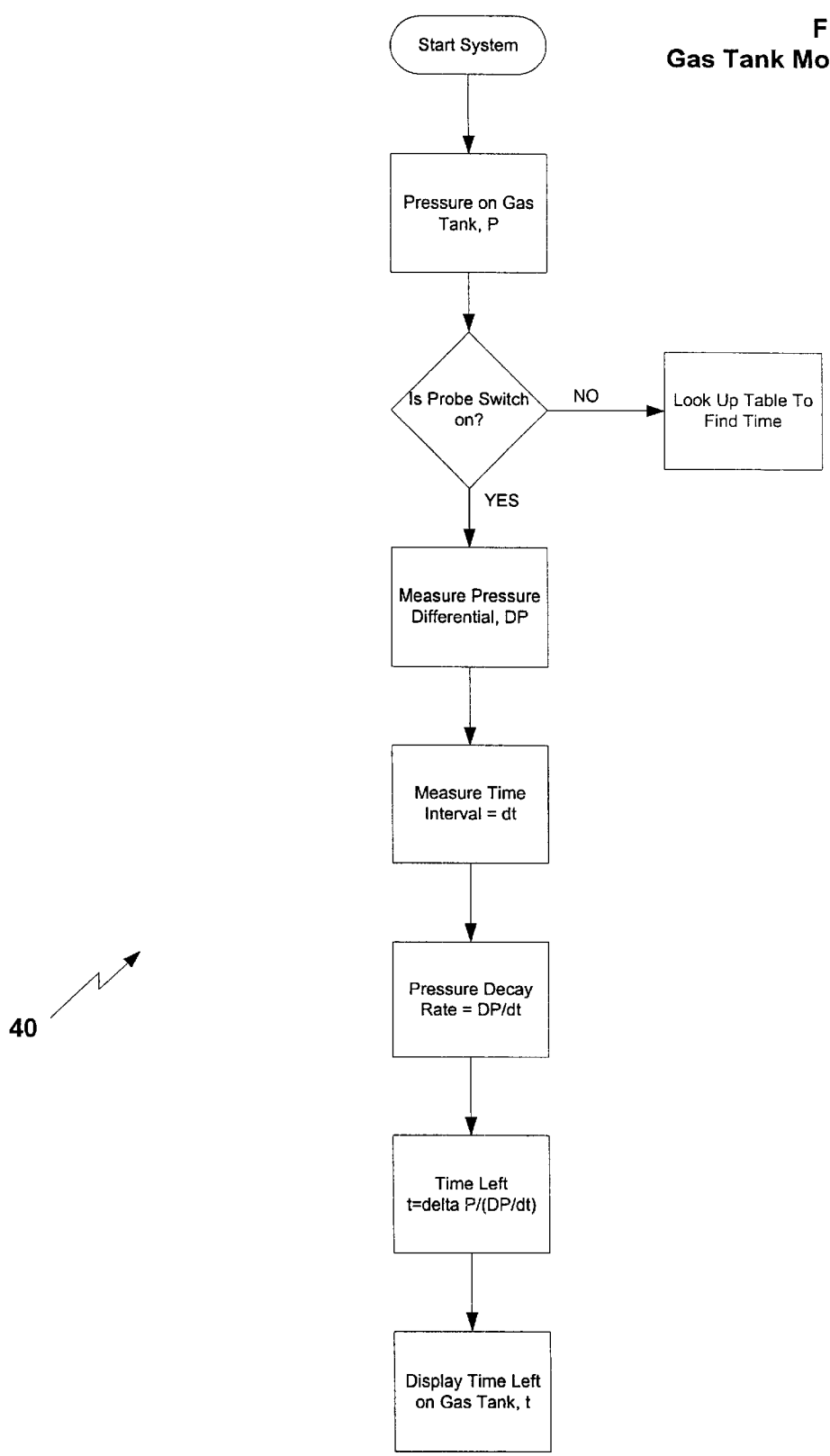
FIG. 3 is a flow diagram of the gas tank monitoring subsystem, in accordance with the principles of the present invention.

Referring now to FIG. 2, a preferred implementation of the temperature feedback system of the present invention is illustrated, designated generally as 36. The temperature feedback control system is programmed to perform the following steps:

At the start of the system a user input setting is read for a target temperature ($T_{user}$). This temperature is utilized for input into a temperature feedback loop, designated 38.

The temperature feedback loop 38 includes the following steps:

The temperature of a tip of the cryosurgical probe ($T_{probe}$) is read. The absolute difference, $T_{diff}$, between $T_{user}$ and $T_{probe}$ is computed and the rate of temperature change of the cryosurgical probe=$T_{delta}=T_{diff}/dt$ is computed. The timing parameters of the pneumatics system that controls the gas flow to the cryosurgical probe is computed based on $T_{delta}$ and $T_{diff}$. The pneumatic system is controlled based on the computed timing to produce an optimal rate of gas flow.

In a particular example of operation, the user can set the target temperature, $T_{user}=-80°$ C. As the system is activated and the probe is placed inside the body there may be a reading of, for example, $T_{probe}=-30°$ C. $T_{diff}$ is internally calculated by the software such that $T_{diff}=abs(T_{probe}-T_{user})=50$. The rate of change of the temperature of the probes is tracked with time, for example, as follows:

$T_{probe-t1}=-15°$ C., $T_{probe}$ at time $t_1$ $T_{probe-t2}=-18°$ C., $T_{probe}$ at time $t_2$ Rate of temperature change, $T_{delta}=(T_{probe-t2}-T_{probe-t1})/(t_2-t_1)$.

The optimum rate of flow is then determined by the following relationship:

Probe operating power=function ($T_{delta}$, $T_{diff}$)

The software module 16 preferably includes a gas supply tank monitoring subsystem, designated generally as 40. System 40 is programmed for performing the following steps:

Pressure data input from the gas supply tank 14 is read and there is a determination as to whether the cryosurgical probe 12 is switched on. If the cryosurgical probe is not switched on a lookup table is checked to determine time left on the supply tank 14. The time left on the gas tank (e.g., in mins.) is computed by looking up a table. This table includes a list of different gas tank pressures and the time left on the gas tank corresponding to these pressures.

If the cryosurgical probe is switched on the pressure differential (DP) is measured. The pressure decay rate defined by the relationship DP/dt is then determined. The time, t, left in the gas supply tank is determined by the relationship $t=\Delta P/(DP/dt)$. An indication of the time left may then be displayed to the user by the user output element of the user interface 22.

In a particular example of the operation of this gas supply tank monitoring subsystem assume that the system has been turned on and the cryosurgical probe is connected. The system will read tank pressure at a predetermined time interval.

For example,
$P_1=5000$ psi at time $t_1=0$ sec.
$P_2=4990$ psi at time $t_2=1$ sec.
$DP=(P_1-P_2)$ psi=10 psi The system will determine the rate of decay by the change in pressure with time:
Rate of decay=$DP/(t_2-t_2)=10$ psi/sec.
The time left on the tank is determined by:
$t=\Delta P/(DP/dt)$
=(4990−3000) psi/10 psi/sec (3000 psi is the set regulated pressure to the pneumatics module.)
=199.0 sec.

Obviously, many modifications and variations of the present invention are possible in light of the above teachings. It is therefore to be understood that within the scope of the appended claims, the invention may be practiced otherwise than as specifically described.

What is claimed and desired to be secured by Letters Patent of the United States is:

1. A software module for a software controlled device for performing cryosurgical procedures on a treatment region with a cryosurgical probe, said software controlled device being responsive to user input settings, comprising:

a temperature feedback control system which is adaptive to the external heat load of a treatment region and utilizes user input settings for determining an optimal rate of gas flow through a cryosurgical probe thereby enabling the user to precisely monitor and deliver a cryosurgical treatment, said temperature feedback control system being programmed to perform the following steps:

a. reading a user input setting for a target temperature ($T_{user}$);

b. utilizing said $T_{user}$ for input into a temperature feedback loop, comprising the steps of:

i. reading a temperature of a cryosurgical probe ($T_{probe}$);

ii. computing $T_{diff}$=absolute difference between $T_{user}$ and $T_{probe}$;

iii. computing the rate of temperature change of the cryosurgical probe=$T_{delta}=T_{probe}/dt$;

iv. computing the timing parameters of a pneumatic system that controls the gas flow to the cryosurgical probe based on $T_{delta}$ and $T_{diff}$; and, v. controlling the pneumatic system based on the computed timing to produce an optimal rate of gas flow.

2. A cryosurgical monitoring system for use with a cryosurgical probe that receives gas from a gas supply, comprising:

a software controlled device for performing cryosurgical procedures, comprising:

a) a software module for providing an interface for monitoring and controlling cryosurgical procedures in response to user input settings and real-time electronics feedback, wherein said software module comprises a temperature feedback system which is adaptive to the external heat load of a treatment region and utilizes user input settings for determining an optimal rate of gas flow through a cryosurgical probe thereby enabling the user to precisely monitor and deliver a cryosurgical treatment, said software module providing control data output, said temperature feedback control system being programmed to perform the following steps:

a. reading a user input setting for a target temperature ($T_{user}$);

b. utilizing said $T_{user}$ for input into a temperature feedback loop, comprising the steps of:

i. reading a temperature of a cryosurgical probe ($T_{probe}$);
ii. computing $T_{diff}$=absolute difference between $T_{user}$ and $T_{probe}$;
iii. computing the rate of temperature change of the cryosurgical probe=$T_{delta}$=$T_{probe}$/dt;
iv. computing the timing parameters of a pneumatic system that controls the gas flow to the cryosurgical probe based on $T_{delta}$ and $T_{diff}$; and,
v. controlling the pneumatic system based on the computed timing to produce an optimal rate of gas flow;

b) an electronics module for receiving said control data output from said software module and providing said real-time electronics feedback, said electronics module providing an electrical output;

c) a pneumatics module for receiving said electrical output and providing a pneumatics module output feedback signal to said electronics module, said pneumatics module providing a pneumatic output to a cryosurgical probe; and, d) a user interface comprising a user input element and a user output element, said user input element for providing said user provided settings to said software module.

3. The cryosurgical monitoring system of claim 2, wherein said pneumatics module comprises a regulator element for providing said pneumatic output to the cryosurgical probe and a pressure sensing element for sensing gas pressure upstream of said regulator element.

4. The cryosurgical monitoring system of claim 2, wherein said software module comprises a gas supply tank monitoring subsystem programmed for performing the following steps:

a) reading pressure data input from a gas supply tank;
b) determining if a cryosurgical probe is switched on;
c) checking a lookup table to determine time if the cryosurgical probe is not switched on;
d) measuring the pressure differential (DP), if the cryosurgical probe is switched on;
e) measuring the time interval, dt, corresponding to DP;
f) determining the pressure decay rate defined by the relationship DP/dt;
g) determining the time, t, left in the gas supply tank by the relationship $\Delta P/(dP/dt)$; and,
h) providing an indication of said time left to said user output element.

5. The cryosurgical monitoring system of claim 2, wherein said software module further comprises a user interface.

* * * * *